Figure 1:
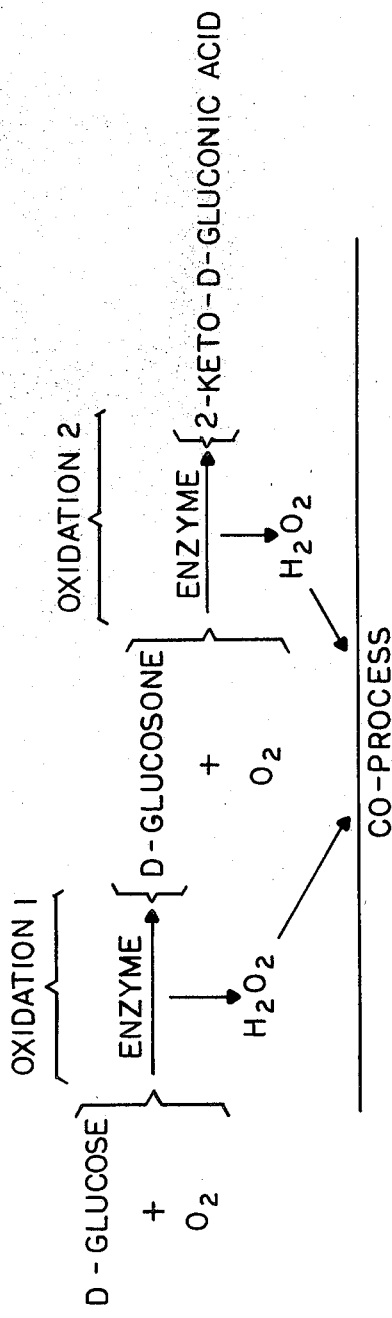

United States Patent [19]

Neidleman et al.

[11] 4,351,902

[45] Sep. 28, 1982

[54] PRODUCTION OF 2-KETO-D-GLUCONIC ACID AND HYDROGEN PEROXIDE

[75] Inventors: Saul L. Neidleman, Oakland; William F. Amon, Jr., Danville; John Geigert, Clayton, all of Calif.

[73] Assignee: Cetus Corporation, Berkeley, Calif.

[21] Appl. No.: 160,122

[22] Filed: Jun. 16, 1980

[51] Int. Cl.$^3$ ............ C12P 7/58; C12P 3/00; C12P 7/26

[52] U.S. Cl. .................. 435/137; 435/148; 435/168

[58] Field of Search ........... 435/42, 105, 136, 137, 435/138, 146, 168

[56] References Cited

U.S. PATENT DOCUMENTS 3,282,795  11/1966  Misenheimer .............. 435/138
4,247,641   1/1981  Neidleman et al. ......... 435/123

OTHER PUBLICATIONS

R. Bently, *The Enzymes*, vol. 7, (1963) pp. 567–587.
Herman, et al., "The Isolation and Characterization of Crystalline D-Arabino-Hexulosonic Acid (2-Keto-D-Gluconic Acid)", *Carbohydrate Research*, vol. 63, (1978), pp. 315–317.
Thompson, *The Modern Inorganic Chemicals Industry*, The Chemical Society, London (1977), pp. 235–242.
Wood, *Methods in Enzymology*, vol. XLI, Academic Press, New York, (1975), pp. 170–173.
Baute et al., "Conversion of Glucose to Cortalcerone via Glucosone by Corticium Caeruleum", *Chem. Abstracts*, vol. 88, No. 7, (1978), p. 273, Abs. No. 47472n.
Vole, et al., "Dicarbonyl Monosaccharides by Enzymatic Oxidation of Aldoses and Ketoses", vol. 90, No. 17, (1979), p. 380, Abs. No. 136263d.
Ratzkowski, et al., "The Quantitative, Differential Determination of Ascorbic Acid and Erythorbic Acid in Foods by Polarography", *Can. Inst. Food. Sci. Technol. Journ.*, vol. 10, (1977), pp. 215–218.
W. Pigman et al., *The Carbohydrates, Chemistry and Biochemistry*, vol. 1A, (1972) pp. 22–39.
Pfeifer, et al., "Production of Calcium 2-Ketogluconate by Fermentation with Species of Pseudomonas", *Ind. Eng. Chem.*, vol. 50, (1958) pp. 1009–1012.
Regna et al., "Kinetics of Transformation of 2-Ketopolyhydroxy Acids", *J. Am. Chem. Soc.*, vol. 66, (1944), pp. 246–250.
Faubl et al., "The Isolation and Characterization of Crystalline D-Arabino-Hexulosonic Acid (2-Keto-D-Gluconic Acid)", *Carbohydr. Res.*, vol. 63, (1978), pp. 315–317.
Hall et al., "Formation of Arabinose, Ribulose and Tartronic Acid from 2-Keto-D-Gluconic Acid", *Biochem. J.*, vol. 60, (1955) pp. 271–274.
Barman, *Enzyme Handbook*, vol. 1, Springer-Verlag, New York, Inc., New York, (1969) pp. 112–114.

*Primary Examiner*—Thomas G. Wiseman
*Attorney, Agent, or Firm*—Fitch, Even, Tabin, Flannery & Welsh

[57] ABSTRACT

A process is described which is useful as a co-process in combination with a process which employs hydrogen peroxide. The process of the invention provides a source of hydrogen peroxide along with a useful co-product, that co-product being 2-keto-D-gluconic acid or products derived therefrom. One of the first and second carbons of D-glucose is oxidized enzymatically to produce hydrogen peroxide and an intermediate product. The other of the first and second carbons of the intermediate product is then oxidized enzymatically to produce hydrogen peroxide and 2-keto-D-gluconic acid. In one form of the invention, the intermediate product is D-glucosone; the final product is 2-keto-D-gluconic acid. In the other form of the invention, the intermediate product is D-glucono-δ-lactone; the final product is a mixture of 2-keto-D-gluconic acid and D-isoascorbic acid.

10 Claims, 2 Drawing Figures

PRODUCTION OF 2-KETO-D-GLUCONIC ACID AND HYDROGEN PEROXIDE

This invention relates generally to processes which produce hydrogen peroxide. More particularly, the invention relates to a co-process for producing such hydrogen peroxide and at the same time producing a useful co-product. In the process of the invention, the useful co-product is 2-keto-D-gluconic acid, numbered according to the Fisher convention.[8]

Many industrial processes employ hydrogen peroxide as a reactant. In some cases, the use of separately manufactured hydrogen peroxide, either in concentrated or dilute form, is feasible and practical. However, there are instances in which the use of separately manufactured hydrogen peroxide is undesirable, either because of high cost (of isolation and concentration, purification, purchase, transport or handling) or because of process/use considerations. In this latter connection, for example, some enzymes used in enzymatic conversion processes which require hydrogen peroxide as a source of oxygen are deleteriously affected by the hydrogen peroxide itself. This is because hydrogen peroxide can oxidize certain critical sites on some enzyme molecules thereby damaging their function and reducing their effectiveness.

For the foregoing reasons, under certain conditions, it is useful to provide a process for producing hydrogen peroxide, this process to be run in conjunction with another process which employs the hydrogen peroxide. This in situ generation of hydrogen peroxide can be designed so that the hydrogen peroxide is utilized at roughly the same rate as it is generated, thereby avoiding an accumulation of high levels of hydrogen peroxide. However, processes for generating hydrogen peroxide known in the prior art are typically not economically efficient.

In U.S. Pat. No. 4,247,641, assigned to the assignee of the present invention, a process is described for producing hydrogen peroxide which also yields (via glucosone) the useful co-product D-fructose. This process has been utilized successfully in combination with an enzymatic process for producing epoxides from alkenes (via the halohydrin) and which employs the hydrogen peroxide generated by the fructose process as a source of oxygen in the epoxidation process. Although this combination of processes operates successfully, it would be desirable for reasons of enhancing market flexibility if alternate commercial co-products could also be produced.

Accordingly, it is an object of the present invention to provide an improved co-process for producing a source of hydrogen peroxide along with a useful chemical co-product of high commercial value.

A more general object of the invention is to provide, in combination with a process employing hydrogen peroxide, a co-process which produces hydrogen peroxide along with a useful co-product.

A further object of the invention is to provide a co-process for providing a source of hydrogen peroxide along with a useful co-product, which co-process provides high yields of hydrogen peroxide.

Figure 2:
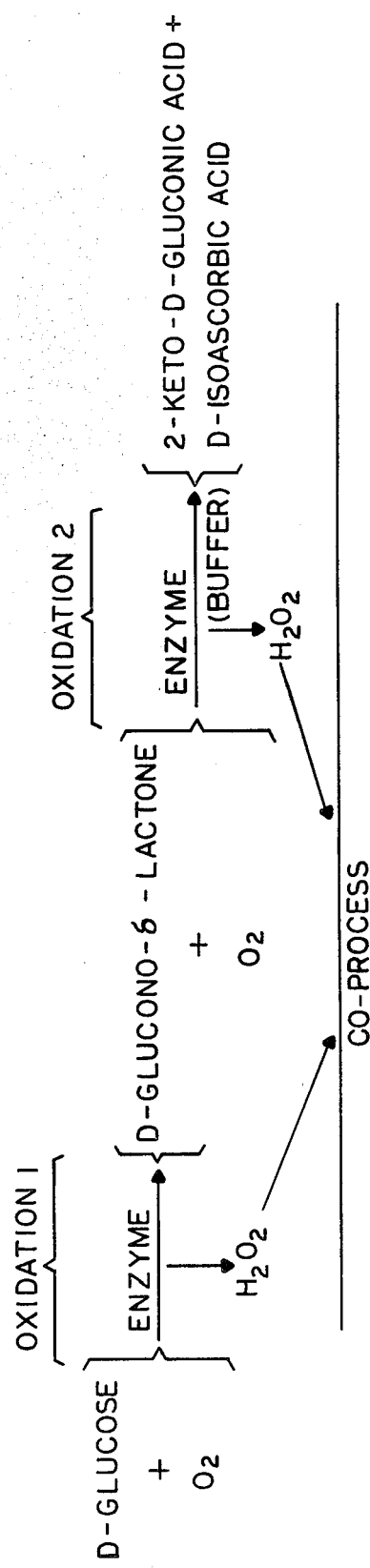

Other objects of the invention will become apparent to those skilled in the art from the following description taken in connection with the accompanying drawings wherein:

FIG. 1 is a schematic depiction of a preferred form of the process of the invention; and FIG. 2 is a schematic depiction of a further embodiment of the invention.

Very generally, the invention provides, in combination with a process employing hydrogen peroxide, a co-process which acts as a source of the hydrogen peroxide and provides, along with it, a useful co-product. D-glucose is enzymatically oxidized at one of the first and second carbons to produce hydrogen peroxide and an intermediate product. The other of the first and second carbons of the intermediate product is then enzymatically oxidized to produce hydrogen peroxide and 2-keto-D-gluconic acid. In one form of the invention, the intermediate product is D-glucosone. In another form of the invention, the intermediate product is D-glucono-δ-lactone. In this latter case, the 2-keto-D-gluconic acid is produced as a mixture with D-isoascorbic acid.

Referring now more particularly to FIG. 1, a preferred form of the invention is shown. The lowermost horizontal line in FIG. 1 represents a process which consumes hydrogen peroxide. Typically, this process will be such that additions of previously isolated hydrogen peroxide are uneconomic or otherwise undesirable. One example of such a process is taught in U.S. Pat. No. 4,247,641, issued Jan. 27, 1981 and assigned to the assignee of the present invention. In that patent, a method is described for the manufacture of epoxides or glycols from olefins. An olefin is contacted with a reaction mixture of a halogenating enzyme, an oxidizing agent and a halide ion source, for a sufficient period to convert the olefin to a halohydrin. The halohydrin is then converted to an epoxide or glycol. Typically, the oxidizing agent is hydrogen peroxide.

An enzyme system is suggested for use in the process described in the aforesaid patent for in situ generation of hydrogen peroxide. Such enzyme systems are well known in the art and include glucose-1-oxidase in the presence of glucose, and methanol oxidase in the presence of methanol. The enzyme for the hydrogen peroxide generating system may be present in the non-immobilized or immobilized state.

With in situ generation of hydrogen peroxide using glucose-1-oxidase or methanol oxidase, co-products include D-glucono-δ-lactone (in the case of glucose-1-oxidase) and formaldehyde (in the case of methanol oxidase). Although each of these co-products is commercially useful, it is conceivable that large scale commercial use of the method for producing epoxides and glycols could result in an amount of co-product being produced by in situ hydrogen peroxide generation which exceeds market demand by a substantial amount.

As previously mentioned, U.S. Pat. No. 4,247,641 describes a co-process which may be used with the epoxide and glycol-producing process described in the previously mentioned U.S. Pat. No. 4,247,641 and which produces, in addition to the hydrogen peroxide, D-fructose.

The process of the present invention is intended to be used as a co-process in parallel and simultaneously with a process which utilizes hydrogen peroxide. In addition to the in situ generation of hydrogen peroxide, the process of the present invention produces 2-keto-D-gluconic acid. The production of 2-keto-D-gluconic acid on a commercial scale has had economic limitations. Heretofore, the existing processes produce 2-keto-D-gluconic acid from D-glucose by fermentation with Pseudomonas species[1] or by fermentation with *Serratia marcescens* (U.S. Pat. No. 3,282,795; 1966). Although the conversion rates and isolated yields of these known processes are high, these processes discard the valuable and useful co-product, hydrogen peroxide, 2-Keto-D-gluconic acid has a variety of commercial uses. As the calcium salt, it is used in photography, principally in developer formulations.[1] Also, it can be readily converted to other commercially useful products such as furfural,[2] D-isoascorbic acid,[3] D-arabinose[4] and D-ribulose.[4] It is also useful as a food preservative.[7]

In the preferred form of the invention as shown in FIG. 1, the process utilizes D-glucose as a starting material. D-glucose may be obtained from any of a variety of relatively low cost sources. In the first step of the co-process of the invention, the D-glucose is reacted with air or oxygen at the second carbon to effect an enzymatically catalyzed oxidation. This first step produces the intermediate product D-glucosone and, in addition, yields hydrogen peroxide. This reaction is preferably conducted in an aqueous solution at about neutral pH, but can be conducted within the pH range of from about 3 to about 8 with the use of appropriate buffers or other pH control. Preferably, the conversion is effected at ambient temperature, but can be conducted within a temperature range of from about 15° C. to about 65° C. Pressure conditions are preferably atmospheric, but can range from below to above atmospheric pressure.

Known enzymes which have the capability of catalyzing this reaction are glucose-2-oxidase or pyranose-2-oxidase. Pyranose-2-oxidase is produced by the microorganism *Polyporus obtusus* and glucose-2-oxidase is produced by the Basidiomycete *Oudemansiella mucida*. The microorganisms may be grown in agitated submerged culture at room temperature by conventional methods. Further details of the sources and preparation of these enzymes are described in the aforesaid U.S. Pat. No. 4,247,641.

Preferably, the enzymes are used in an immobilized form, although free enzymes can also be used. Processes for enzyme immobilization are familiar to those skilled in the art and consist of reacting a solution of the enzyme with one of a broad range of surface-treated or untreated organic and inorganic supports. Included amoung these are polyacrylamide, ethylenemaleic acid copolymers, methacrylic-based polymers, polypeptides, styrene-based polymers, agarose, cellulose, dextran, silica, porous glass beads, charcoal or carbon black, hydroxy appatite, and aluminum or titanium hydroxide. Enzymes in this form have increased stability, extended life and usefulness, and recoverability. Reactions employing immobilized enzymes may be run in columns or reaction tanks or other suitable reactors.

After producing the intermediate product D-glucosone, a further reaction takes place wherein the D-glucosone is oxidized at the first carbon in an enzymatically catalyzed oxidation to form hydrogen peroxide and 2-keto-D-gluconic acid. The enzyme glucose-1-oxidase, produced for example from the microorganism *Aspergillus niger*, reacts with D-glucosone to yield 2-keto-D-gluconic acid and hydrogen peroxide[9]. The pressure, temperature and pH ranges for the second step of the reaction are essentially the same as those described in connection with the first step.

The result of the two step conversion process is that two moles of hydrogen peroxide and one mole of 2-keto-D-gluconic acid are produced for every mole of D-glucose converted. In addition, the generation of the hydrogen peroxide occurs in an aqueous solution at temperatures and pressures which are easily accommodated to parallel and simultaneous operation with other processes in which hydrogen peroxide is required. Thus, by combining the in situ hydrogen peroxide generating process of this invention with the process for producing epoxides and glycols from olefins as described above, olefin epoxide production can occur, and the useful co-product 2-keto-D-gluconic acid is also produced.

Referring now to FIG. 2, a second embodiment of the invention is shown. As was the case in the first embodiment of the invention, the co-process illustrated in FIG. 2 is a two-step process. In the first step one of the first and second carbons of D-glucose is oxidized. However, instead of the second carbon being oxidized as in the case in the co-process of the embodiment of FIG. 1, rather, the first carbon of D-glucose is oxidized in the first step in the embodiment of FIG. 2. This is accomplished by utilizing the enzyme glucose-1-oxidase under conditions essentially the same as those described in connection with FIG. 1. The result is the production of the intermediate product D-glucono-δ-lactone.

The second step of the embodiment of FIG. 2 operates to oxidize the second carbon of the D-glucono-δ-lactone in an enzymatic oxidation in which the enzyme pyranose-2-oxidase is employed. The reaction, because D-glucono-δ-lactone is an acidic substance, requires pH control and therefore buffering in order to keep the reaction mixture closer to a neutral pH for the reaction with the pyranose-2-oxidase. The resulting product is a mixture of 2-keto-D-gluconic acid and D-isoascorbic acid. In both enzymatic oxidation steps of the embodiment of FIG. 2, hydrogen peroxide is also produced. Therefore, for every mole of D-glucose utilized, two moles of hydrogen peroxide are produced as well as one mole equivalent of a mixture of 2-keto-D-gluconic acid and D-isoascorbic acid.

In the embodiments of both FIGS. 1 and 2, air or oxygen is added for both the first and second step reactions. Bracketing in each of the figures indicates products and necessary reactants for the first and second steps.

D-Isoascorbic acid is a commercial product useful as an anti-oxidant for food products, or as an intermediate for producing other useful end products such as furfural. In fact, the mixture of the 2-keto-D-gluconic acid and D-isoascorbic acid can be converted to furfural without separation of the two products. Although both of the oxidations utilized in the process of the embodiment of FIG. 2 are individually known in the prior art, [5,6] these oxidations have never been combined in a single process to yield a mixture of 2-keto-D-gluconic acid and D-isoascorbic acid. Moreover, it is unlikely that such a process has occurred but been undiscovered in nature, since the enzymes glucose-1-oxidase and pyranose-2-oxidase are from unrelated microorganisms.

The following examples are set forth to illustrate specific applications of the invention. However, the scope of the invention is intended to be defined by the appended claims and the following examples are not intended to limit the scope of the invention in any way.

EXAMPLE 1

This example demonstrates the production of 2-keto-D-gluconic acid (2KGA) from D-glucosone using glucose-1-oxidase. The example demonstrates the second oxidation of FIG. 1. In this example, the utilization of the produced hydrogen peroxide in a co-process is simulated by decomposition with the enzyme, catalase.

D-glucosone (1 g) is added to 20 ml of 0.2 M potassium phosphate buffer (pH 6.0) in a 100 ml Pyrex flask and the sugar solution stirred. Oxygen gas is continuously bubbled into the flask. Catalase (1 mg) purchased from Sigma Chemical Company (No. C10, purified powder from bovine liver) is added. Glucose-1-oxidase (0.1 ml; 1000 units/ml) purchased from Sigma Chemical Company (No. G6500, prepared from *Aspergillus niger*) is added.

Samples are withdrawn and analyzed for residual D-glucosone and produced 2-keto-D-gluconic acid. High-performance liquid chromatography is used to analyze the results. A μ-Bondapak-Carbohydrate column, purchased from Waters Associates, is attached to a Waters Associates HPLC instrument containing dual detectors—refractive index and UV/VIS ($\lambda$192 nm). The mobile phase is 20% aqueous acetonitrile containing 0.003 M potassium phosphate buffer (pH 6) and is passed through the column at 2 ml/min.

Authentic samples of D-glucosone (prepared enzymatically from *Polyporus obtusus* as described in U.S. Pat. No. 4,247,641 and 2KGA (purchased from Sigma Chemical Company) are run for comparison. D-glucosone has a retention time at 15 minutes, and 2KGA at 11 minutes. Residual substrate and product formed are quantitated using peak areas at UV $\lambda$192 nm.

The following results are obtained:

| Reaction Time | Approximate Yield of 2KGA | Approximate % of D-Glucosone Converted to 2KGA |
| --- | --- | --- |
| 0.4 hr | 22 mg | 2 |
| 2 | 343 | 33 |
| 6 | >1050 | >96 |

Essentially complete conversion of D-glucosone to 2-keto-D-gluconic acid is obtained.

EXAMPLE II

This example demonstrates the production of 2-keto-D-gluconic acid from D-glucose via D-glucosone. In this example, utilization of the produced hydrogen peroxide in a co-process is simulated by decomposition with the enzyme, catalase.

D-glucose (1 g) is added to 20 ml of 0.2 M potassium phosphate buffer (pH 6) in a 100 ml Pyrex flask and the sugar solution stirred. Oxygen gas is continuously bubbled into the flask. 3 mg of catalase (Sigma Chemical Company, purified powder from bovine liver) is added. Agarose-immobilized pyranose-2-oxidase (5 g wet weight) prepared as below is also added to the flask.

To prepare the enzyme, mycelial pads of *Polyporus obtusus* ATCC No. 26733 are grown on yeast/malt extract agar slants as follows: yeast extract (3 g), malt extract (3 g), agar (20 g), peptone (5 g) and glucose (10 g) are added to distilled water (1 liter) and the pH is adjusted to 6.7. The medium is sterilized at 121° C. for 15 minutes. The pH is then adjusted to 6.4. The organism is inoculated on the agar slants and grown for 7 days at 25° C. The slant-grown organism is then used to inoculate yeast/malt extract medium (20 ml medium in 125 ml Erlenmeyer flask), prepared as above (but no agar added). The organism is grown for 9 days on a rotary shaker at 25° C. The culture is vacuum filtered through No. 541 Whatman paper in a Buchner funnel. The mycelia, retained on the filter paper, contain the enzyme.

The mycelia obtained from 400 ml of culture are washed twice with 0.05 M potassium phosphate buffer at pH 7.0. The mycelia are then placed in a Waring blender which contains 70 ml of 0.05 M potassium phosphate buffer at 7.0, and then homogenized for 3 minutes. The mixture is then centrifuged at 6000 rpm for 20 minutes and the supernatant decanted from the solids. To the supernatant, placed in a 500 ml Erlenmeyer flask, 19 g of polyethylene glycol (weight 4000) is added and the solution stirred for 30 minutes. The suspension is then centrifuged at 7000 rpm for 20 minutes. The supernatant is decanted off and discarded. 15 ml of 0.2 M sodium chloride plus 15 ml 0.05 M potassium phosphate buffer at pH 7.0 are then added to the precipitate and vortexed. The solution is allowed to stand for 30 minutes, during which time a precipitate forms. The mixture is centrifuged at 14000 rpm for 20 minutes. An opaque white supernatant containing cell-free, purified enzyme is decanted off.

Immobilization of the enzymes on agarose may be accomplished as follows: the cell-free purified enzyme is dialyzed against 500 ml of distilled water overnight. The 5 ml of 0.1 M sodium bicarbonate at pH 8.0 is added. To this solution, 5 g of Activated CH-Sepharose 4B (washed and re-swelled on a sintered glass filter using 500 ml of 1 mM HCl) is added. Using an end-over-end mixer, the gel suspension is mixed for 1 hour at 25° C. The gel suspension is then washed first with 40 ml of 0.1 M sodium bicarbonate at pH 8.0, then with 40 ml of 0.05 M Tris buffer at pH 8.0 containing 0.5 M sodium chloride, and then with 0.5 M sodium formate buffer at pH 4.0 also containing 0.5 M sodium chloride.

Samples of the reaction mixture are withdrawn at varying times and analyzed for D-glucose and D-glucosone using the HPLC method described in Example 1. The peak areas of the peaks at retention time 10 min. (D-glucose) and at retention time 15 min. (D-glucosone) are quantitated using the refractive index (RI) detector.

The following results are obtained:

| Reaction Time | Approximate Yield of D-Glucosone | Approximate % of D-Glucose Converted to D-Glucosone |
| --- | --- | --- |
| 0.1 hr. | 30 mg | 3 |
| 1 | 418 | 42 |
| 2 | 745 | 75 |
| 4 | >996 | >99 |

Essentially complete conversion of D-glucosone is obtained.

At this point, glucose-1-oxidase (0.1 ml; 1000 units/ml) purchased from Sigma Chemical Company (prepared from *Aspergillus niger*) is added.

Samples of the reaction mixture are withdrawn at varying times and analyzed for D-glucosone and 2-keto-D-gluconic acid using the HPLC method described in Example 1. The peak areas of the peaks at retention time 15 min. (D-glucosone) and at retention time 11 min. (2KGA) are quantitated using the UV detector set at $\lambda$192 nm.

The following results are obtained:

| Reaction Time | Approximate Yield of 2KGA | Approximate % of D-Glucosone Converted to 2KGA |
|---|---|---|
| 0.4 hr. | 18 mg | 2 |
| 2 | 287 | 30 |
| 6 | >993 | >96 |

Essentially complete conversion of D-glucosone to 2-keto-D-gluconic acid is obtained.

Thus, essentially complete conversion of D-glucose to 2KGA is obtained.

EXAMPLE III

This example demonstrates the production of both 2-keto-D-gluconic acid and D-isoascorbic acid from D-glucose via D-glucono-δ-lactone. In this example, the produced hydrogen peroxide is decomposed with the enzyme, catalase.

D-glucose (1 g) is added to 20 ml of 0.2 M potassium phosphate buffer (pH 6) in a 100 ml Pyrex flask and the sugar solution stirred. Oxygen gas is bubbled continuously into the flask. 3 mg of catalase (Sigma Chemical Company, purified powder from bovine liver) is added. Glucose-1-oxidase (0.1 ml; 1000 units/ml) purchased from Sigma Chemical Company (prepared from *Aspergillus niger*) is added.

Samples of the reaction mixture are withdrawn at varying times and analyzed for D-glucose and D-glucono-δ-lactone using the HPLC method described in Example I. Authentic samples of D-glucose (purchased from Applied Sciences Inc.) and D-glucono-δ-lactone (purchased from Pfaltz and Bauer Company) are run for comparison. The peak areas of the peaks at retention time 10 min. (D-glucose) and at retention time 5 min. (D-glucono-δ-lactone) are quantitated using the refractive index (R1) detector.

The following results are obtained:

| Retention Time | Approximate Yield of D-Glucono-δ-lactone | Approximate % of D-Glucose Converted to D-Glucono-δ-lactone |
|---|---|---|
| 0.1 hr | 48 mg | 5 |
| 2 | 436 | 44 |
| 6 | >1003 | >98 |

Essentially complete conversion of D-glucose to D-glucono-δ-lactone is obtained.

At this point, agarose-immobilized pyranose-2-oxidase (6 g wet weight) prepared as in Example II is added.

Samples of the reaction mixture are withdrawn at varying times and analyzed for D-isoascorbic acid, D-glucono-δ-lactone and 2KGA using the HPLC method described in Example I. The peak areas of the peaks at retention time 5 min. (D-glucono-δ-lactone), at retention time 11 min. (2KGA) and at retention time 6 min. (D-isoascorbic acid) are quantitated using the UV detector set at λ192 nm.

The following results are obtained:

| Reaction Time | Approximate Yield of 2KGA | Approximate Yield of D-Isoascorbic Acid | Approximate % of D-Glucono-δ-lactone Converted to 2KGA and D-Isoascorbic Acid |
|---|---|---|---|
| 0.2 hr. | 53 | 22 | 8 |
| 3 | 302 | 278 | 55 |
| 8 | 511 | >473 | >92 |

Essentially complete conversion of D-glucono-δ-lactone to an approximate 1:1 molar mix of 2KGA and D-isoascorbic acid is obtained.

Thus, essentially complete conversion of D-glucose to 2KGA and D-isoascorbic acid is obtained.

EXAMPLE IV

This example demonstrates the production of 2-keto-D-gluconic acid from D-glucose via D-glucosone, and the co-production of propylene bromohydrin and epoxide by consuming the produced hydrogen peroxide.

In this example, hydrogen peroxide production is coupled to the production of propylene bromohydrin, an intermediate in propylene oxide synthesis according to concepts detailed in U.S. Pat. No. 4,247,641. The reaction of D-glucose and the immobilized pyranose-2-oxidase of *Polyporus obtusus* ATCC No. 26733 to yield D-glucosone and hydrogen peroxide is coupled to the reaction of immobilized seaweed peroxidase from Coralina sp. in the presence of bromide and propylene to yield propylene bromohydrin. The end result of this coupled reaction, then, is the production of D-glucosone for subsequent 2KGA production and of additional propylene bromohydrin, readily converted to propylene oxide.

Cell-free, purified seaweed peroxidase enzyme is prepared as follows:

Coralina sp. obtained along the coast of La Jolla, Calif., is ground in a Virtis 45 homogenizer for 5 minutes in distilled water. The homogenate is spun at 20,000 rpm for 20 minutes. The supernatant is decanted and saved. The pellet is resuspended in distilled water and recentrifuged. This supernatant and previous supernatant are combined. The solution is brought first to 33%, then to 55% saturation in ammonium sulfate. Centrifugation and separation of pellet is performed at each step. The 33%–55% pellet fraction is passed through a DEAE column using a 0.3 M to 1 M phosphate buffer (pH 6.0) gradient. The fraction which elutes at 1 M is dialyzed against 20 mM phosphate buffer (pH 6) overnight.

The immobilized seaweed peroxidase is prepared as follows:

Glass beads (obtained from Sigma Chemical Company, PG-700-200) are activated by suspending 1 g of glass beads in 18 ml of deionized water. 2 ml of 10% (v/v) α-amino-propyltriethoxy silane are added and the pH of the mixture is adjusted to 3–5 with 6 N HCL. The mixture is shaken at 75° C. for two hours. The glass beads are then vacuum dried overnight at 80° C. 3.2 ml of purified Coralina sp. enzyme, prepared as above, and 50 mg. of water-soluble carbodiimide are added to the glass beads. The pH is adjusted to 4.5, and the mixture is then shaken at 4° C. overnight. The product (enzyme-coated beads) is washed with water. The activity is measured as 2 monochlorodimedon units/g of beads.

Immobilized pyranose-2-oxidase on agarose is prepared as in Example II from 10 ml of cell-free, purified enzyme.

A reaction mixture containing the following ingredients is set up in a 100 ml Pyrex flask:
(a) 1 g seaweed peroxidase-coated glass beads,
(b) the immobilized pyranose-2-oxidase prepared above,
(c) 700 mg potassium bromide, and
(d) 20 ml of 0.20 potassium phosphate buffer, pH 6.0.

Both propylene and oxygen are bubbled into the flasks continuously. The reaction is initiated with 0.5 g D-glucose. After 10 hours, the reaction mixture is sampled and analyzed for D-glucose and D-glucosone using the HPLC method described in Example II. The produced propylene bromohydrin is also analyzed as follows:

Finnigan 4021 gas chromatograph-mass spectrometer (GCMS); 6 foot×¼ inch coiled glass column packed with Tenax-GC (80/100 mesh); 30 ml/minute helium flow; column temperature is set at 200° C. Propylene bromohydrin has a retention time of 10 minutes. Authentic sample of propylene bromohydrin is purchased from Pfaltz and Bauer, Inc. Peak areas measured by a flame ionization detector (FID) is used for quantitation.

The HPLC analysis shows that essentially complete conversion of D-glucose to D-glucosone has occured. 501 mg of D-glucosone is measured.

The GCMS analysis shows that essentially complete consumption of hydrogen peroxide to yield propylene bromohydrin has occurred. 363 mg of propylene bromohydrin is measured.

At this point, glucose-1-oxidase purchased from Sigma Chemical Company is immobilized on Sepharose and added to the reaction flask.

Immobilized glucose-1-oxidase is prepared as follows:

The glucose-1-oxidase (1000 units/ml) is purchased from Sigma Chemical Company. The insoluble beads of AH-Sepharose 4B are obtained from Pharmacia Fine Chemical Company. Both enzyme and beads are adjusted to pH 5.0. To immobilize the enzyme onto the beads, 0.2 ml glucose-1-oxidase and 1 ml beads are mixed. The coupling reaction is initiated by the addition of 2 ml N-cyclohexyl-N' (2-(4-methyl-morpholino)-ethyl) carbodiimide solution (100 mg/2 ml). The reaction mixture is incubated at 4° C. overnight. The beads are then washed with 0.03 M phosphate buffer (pH 4.4). The glucose oxidase-AH-Sepharose 4B beads are stored at 4° C. for use.

After 10 additional hours of reaction, the reaction mixture is sampled and analyzed for D-glucosone and 2KGA using the HPLC method described in Example II. The additional production of propylene bromohydrin is also analyzed as described in part 1 of this Example.

The HPLC analysis shows that essentially complete conversion of D-glucosone to 2KGA has occurred. 484 mg of 2KGA is measured.

The GCMS analysis shows that essentially complete consumption of this second portion of hydrogen peroxide has occurred. 347 mg of additional propylene bromohydrin is measured.

Thus, the 2 moles of hydrogen peroxide produced from each mole of D-glucose is essentially completely consumed to produce propylene bromohydrin (710 mg total; equals the approximate consumption of >95% of the hydrogen peroxide produced). The produced propylene bromohydrin is readily converted to propylene epoxide as described in U.S. Pat. No. 4,247,641.

EXAMPLE V

This example demonstrates the production of 2-keto-D-gluconic acid and D-isoascorbic acid from D-glucose via D-glucono-δ-lactone, and the co-production of propylene bromohydrin and epoxide by consuming the produced hydrogen peroxide.

In this example, hydrogen peroxide production is coupled to the production of propylene bromohydrin, an intermediate in propylene oxide synthesis according to concepts detailed in U.S. Pat. No. 4,247,641. The reaction of D-glucose and the immobilized glucose-1-oxidase of *Aspergillus niger* to yield D-glucono-δ-lactone and hydrogen peroxide is coupled to the reaction of immobilized seaweed peroxidase from Coralina sp. in the presence of bromide and propylene to yield propylene bromohydrin. The end result of this coupled reaction, then, is the co-production of D-glucono-δ-lactone for subsequent 2KGA and D-isoascorbic acid and of additional propylene bromohydrin, readily converted to propylene oxide.

Immobilized, cell-free, purified seaweed peroxidase enzyme is prepared as in Example IV.

Immobilized glucose-1-oxidase is prepared as follows:

The glucose-1-oxidase (1000 units/ml) is purchased from Sigma Chemical Company. The insoluble beads of AH-Sepharose 4G are obtained from Pharmacia Fine Chemical Company. Both enzyme and beads are adjusted to pH 5.0. To immobilize the enzyme onto the beads, 0.2 ml glucose-1-oxidase and 1 ml beads are mixed. The coupling reaction is initiated by the addition of 2 ml N-cyclohexyl-N'(2-(4-methyl-morpholino)-ethyl) carbodiimide solution (100 mg/2 ml). The reaction mixture is incubated at 4° C. overnight. The beads are then washed with 0.03 M phosphate buffer (pH 4.4). The glucose oxidase-AH-Sepharose 4B beads are stored at 4° C. for use.

A reaction mixture containing the following ingredients is set up in a 100 ml Pyrex flask:
(a) 1 g seaweed peroxidase-coated glass beads,
(b) the immobilized glucose-1-oxidase prepared above,
(c) 700 mg potassium bromide, and
(d) 20 ml of 0.20 potassium phosphate buffer, pH 6.0.

Both propylene and oxygen are bubbled into the flasks continuously. The reaction is initiated with 0.5 g D-glucose.

After 10 hours, the reaction mixture is sampled and analyzed for D-glucose and D-glucono-δ-lactone using the HPLC method described in Example III. The produced propylene bromohydrin is analyzed using the GCMS method described in Example IV.

The HPLC analysis shows that essentially complete conversion of D-glucose to D-glucono-δ-lactone has occurred. 482 mg of D-glucono-δ-lactone is measured.

The GCMS analysis shows that essentially complete consumption of hydrogen peroxide to yield propylene bromohydrin has occurred. 352 mg of propylene bromohydrin is measured.

At this point, immobilized pyranose-2-oxidase, prepared as in Example IV, is then added.

After 12 additional hours of reaction, the reaction mixture is sampled and analyzed for 2KGA and D-isoascorbic acid using the HPLC method described in Example III. The additional production of propylene bromohydrin is also analyzed using the GCMS method described in Example IV.

The HPLC analysis shows that essentially complete conversion of D-glucono-δ-lactone to 2KGA and D-isoascorbic acid has occurred. 248 mg of 2KGA and 222 mg D-isoascorbic acid are measured.

The GCMS analysis shows that essentially complete consumption of the second portion of hydrogen peroxide has occurred. 336 mg of additional propylene bromohydrin is measured.

Thus, the 2 moles of hydrogen peroxide produced from each mole of D-glucose are essentially completely consumed to produce propylene bromohydrin (688 mg total; equals the approximate consumption of >90% of the hydrogen peroxide produced).

The produced propylene bromohydrin is readily converted to propylene epoxide as described in U.S. Pat. No. 4,247,641.

It may be seen, therefore, that the invention provides a means by which hydrogen peroxide may be efficiently generated in situ to provide a source of hydrogen peroxide for a particular process requiring it. The hydrogen peroxide is generated by a totally enzymatic process which also produces a useful end product. The useful end product, namely, 2-keto-D-gluconic acid, alone or in a mixture with D-isoascorbic acid, is useful by itself or as a precursor product for many other types of products. Thus, a ready source of hydrogen peroxide is provided for those reactions which require it by means of a low cost process which, in and of itself, results in production of a useful co-product.

Various modification of the invention in addition to those shown and described herein will become apparent to those skilled in the art from the foregoing description and accompanying drawings. Such modifications are intended to fall within the scope of the appended claims.

| U.S. PATENTS | |
|---|---|
| 3,282,795 | 1966 T. J. Misenheimer |
| U.S. Pat. Application Ser. No. 42,219 | 1981 S. L. Neidleman et al. |

REFERENCES

1. V. F. Peiffer et al., *Ind. Eng. Chem.*, 50:1009–12 (1958)
2. P. P. Regna et al., *J. Amer. Chem. Soc.*, 66:246–50 (1944)
3. H. Faubl et al., *Carbohydr. Res.*, 63:315–17 (1978)
4. A. N. Hall et al., *Biochem. J.*, 60:271–74 (1955)
5. T. E. Barman, *Enzyme Handbook*, Volume 1 (1969)
6. W. A. Wood, *Methods in Enzymology*, Volume 41 (1975)
7. C. Ratzkowski et al., *Can. Inst. Food Sci. Technol. Jour.*, 10:215–218 (1977)
8. W. Pigman, et al., *The Carbohydrates, Chemistry and Biochemistry*, Volume 1A, 22 (1972)
9. R. Bentley, *The Enzymes* 7, 567 (1963).

What is claimed is:

1. A process for producing hydrogen peroxide and 2-keto-D-gluconic acid, comprising, reacting D-glucose in aqueous solution with oxygen and a first enzyme selected from the group consisting of pyranose-2-oxidase, glucose-2-oxidase, and glucose-1-oxidase to catalize oxidation of one of the first and second carbons of the D-glucose and produce an intermediate product comprising D-glucosone or D-glucono-δ-lactone, reacting the intermediate product in aqueous solution with oxygen and a second enzyme selected from the group consisting of pyranose-2-oxidase and glucose-1-oxidase to catalyze oxidation of the other of the first and second carbons of the intermediate product and produce hydrogen peroxide and 2-keto-D-gluconic acid, and recovering the 2-keto-D-gluconic acid.

2. The process of claim 1 wherein D-isoascorbic acid is co-produced with the 2-keto-D-gluconic acid.

3. The process of claim 1 wherein the intermediate product formed is D-glucosone.

4. The process of claim 3 wherein the D-glucosone is formed using an enzyme selected from the group consisting of glucose-2-oxidase and pyranose-2oxidase.

5. The process of claim 3 wherein the D-glucosone is oxidized to 2-keto-D-gluconic acid using the enzyme glucose-1-oxidase.

6. The process of claim 1 wherein the intermediate product formed is D-glucono-δ-lactone.

7. The process of claim 6 wherein the D-glucono-δ-lactone is formed using the enzyme glucose-1-oxidase.

8. The process of claim 6 wherein the D-glucono-δ-lactone is oxidized to 2-keto-D-gluconic acid using the enzyme pyranose-2-oxidase resulting in co-production of D-isoascorbic acid.

9. A new process for producing hydrogen peroxide and 2-keto-D-gluconic acid, comprising, reacting D-glucose in aqueous solution with oxygen and a first enzyme selected from the group consisting of pyranose-2-oxidase and glucose-2-oxidase to catalize oxidation of the second carbon of the D-glucose and produce D-glucosone, reacting the D-glucosone in aqueous solution with oxygen and glucose-1-oxidase to catalyze oxidation of the first carbon of the D-glucosone and produce hydrogen peroxide and 2-keto-D-gluconic acid, and recovering the 2-keto-D-gluconic acid.

10. A process for producing hydrogen peroxide and 2-keto-D-gluconic acid, comprising, reacting D-glucose in aqueous solution with oxygen and glucose-1-oxidase to catalize oxidation of the first carbon of the D-glucose and produce D-glucono-δ-lactone, reacting the D-glucono-δ-lactone in aqueous solution with oxygen and pyranose-2-oxidase to catalyze oxidation of the second carbon of the D-glucono-δ-lactone and produce hydrogen peroxide, 2-keto-D-gluconic acid, and D-isoascorbic acid, and recovering the 2-keto-D-gluconic acid.

* * * * *